United States Patent
Paul et al.

(10) Patent No.: US 9,226,757 B2
(45) Date of Patent: Jan. 5, 2016

(54) BONE REMOVAL INSTRUMENT

(75) Inventors: David C. Paul, Phoenixville, PA (US);
William S Rhoda, Media, PA (US);
Donald Kolletzki, Perkiomenville, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 318 days.

(21) Appl. No.: 13/170,313

(22) Filed: Jun. 28, 2011

(65) Prior Publication Data
US 2013/0006249 A1    Jan. 3, 2013

(51) Int. Cl.
*A61B 17/00* (2006.01)
*A61B 17/16* (2006.01)

(52) U.S. Cl.
CPC .................................. *A61B 17/1611* (2013.01)

(58) Field of Classification Search
CPC .................. A61B 17/1604; A61B 17/1611
USPC .................................. 600/564; 606/79, 83, 99
See application file for complete search history.

(56) References Cited

U.S. PATENT DOCUMENTS

| 3,590,808 | A | | 7/1971 | Muller |
| 3,902,498 | A | | 9/1975 | Niederer |
| 4,368,734 | A | | 1/1983 | Banko |
| 4,777,948 | A | * | 10/1988 | Wright ............................ 606/83 |
| 5,009,661 | A | | 4/1991 | Michelson |
| 5,026,375 | A | | 6/1991 | Linovitz |
| 5,385,570 | A | | 1/1995 | Chin |
| 5,653,713 | A | * | 8/1997 | Michelson ...................... 606/83 |
| 5,766,177 | A | * | 6/1998 | Lucas-Dean et al. ........... 606/83 |
| 5,961,531 | A | * | 10/1999 | Weber et al. .................. 606/167 |
| 7,922,723 | B2 | | 4/2011 | Michelson |
| 2011/0106065 | A1 | | 5/2011 | Tontarra et al. |

* cited by examiner

*Primary Examiner* — Christopher Beccia
*Assistant Examiner* — Diana S Jones

(57) ABSTRACT

Improved spinal instruments are provided. In particular, the present application relates to an improved rongeur that allows for multiple bites of bone to be performed in a patient before removing the rongeur from the patient. The rongeur includes a lower shaft and an upper shaft slidable relative to the lower shaft. The lower shaft and upper shaft form a jaw mechanism that can take multiple bites of bone, which can be deposited in a storage cavity formed in the upper shaft. To assist in removing the bone from within the storage cavity, an internal plunger mechanism can be provided that is actuated by a finger hold. In addition, at least portions of the upper shaft are detachable from the lower shaft such that the upper shaft can be thoroughly cleaned and re-used if desired.

15 Claims, 3 Drawing Sheets

US 9,226,757 B2

BONE REMOVAL INSTRUMENT

FIELD OF THE INVENTION

The present application generally relates to surgical instruments, and more particularly, to instruments for removing bone material.

BACKGROUND OF THE INVENTION

During spinal surgeries, a rongeur can be used to remove bone. Typically, rongeurs may be designed to take a single bite of bone at a time. After each bite, the rongeur is taken out of a surgical site to retrieve the bone material. Removing the rongeur out of the body after each bite is inefficient and increases the risk of contamination to the patient. Furthermore, rongeurs are often difficult to clean.

Thus, there remains a need for an improved rongeur that has increased efficiency, cleanliness and provides greater safety to a patient.

SUMMARY OF THE INVENTION

In some embodiments, a rongeur is provided comprising a handle; a lower shaft operably connected to the handle; and an upper shaft slidable relative to the lower shaft, wherein the upper shaft includes an internal storage cavity for receiving bone tissue material and an internal plunger mechanism configured to push out bone tissue material from the internal storage cavity.

In other embodiments, a rongeur is provided including a handle; a lower shaft operably connected to the handle; and an upper shaft slidable relative to the lower shaft, wherein the upper shaft includes an internal storage cavity and an internal plunger mechanism positioned near a proximal portion of the upper shaft, wherein the handle and the internal plunger mechanism are capable of one-handed operation.

In other embodiments, a method is provided comprising forming an incision in a body of a patient; inserting a rongeur through the incision, wherein the rongeur includes a jaw mechanism formed by a lower shaft and an upper shaft, and wherein the upper shaft includes a storage cavity adjacent an internal plunger mechanism; using the jaw mechanism to take two or more bites out of a bone, wherein at least some bone tissue from the bone is deposited in the storage cavity; removing the rongeur from the body of the patient; and utilizing the internal plunger mechanism to push out and expel bone tissue material within the storage cavity in the upper shaft.

DETAILED DESCRIPTION OF THE ILLUSTRATED EMBODIMENTS

Detailed embodiments of the invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The present application generally relates to surgical instruments, and in particular, to improved rongeurs. The improved rongeurs include a storage cavity that can accommodate bone tissue material from multiple bites of bone, thereby reducing the need to remove the rongeur from the patient's body after each bite of bone. The improved rongeur also advantageously provides a simple mechanism that dislodges and expels any bone tissue material from the storage cavity. Advantageously, the storage cavity of the improved rongeur is capable of being detached and thoroughly cleaned.

Figure 1:
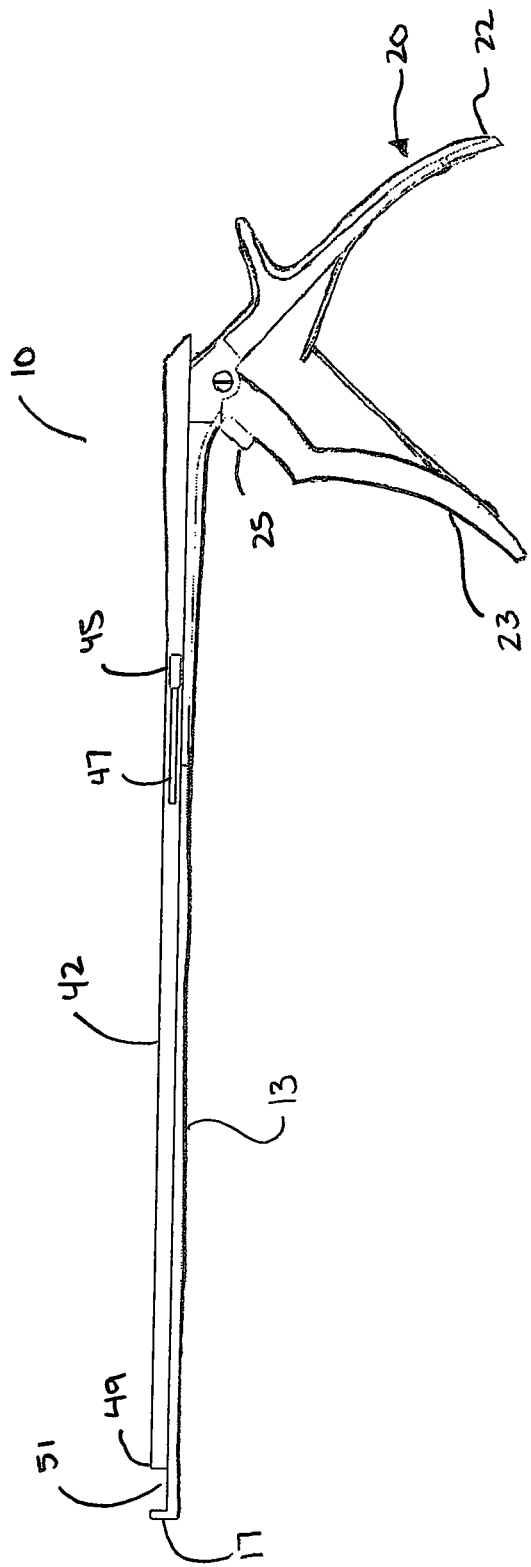
FIG. 1 is a side view of a rongeur according to some embodiments of the present application.
Figure 2:
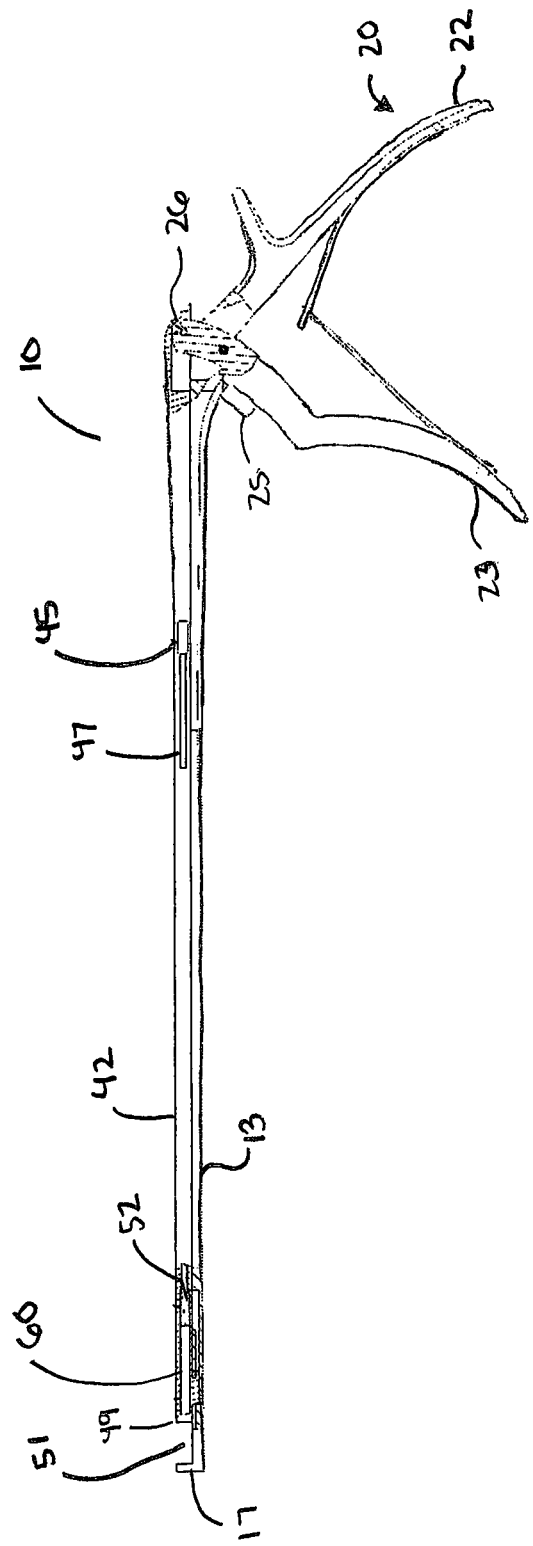
FIG. 2 is a cross-sectional view of a rongeur according to some embodiments of the present application.

FIG. 1 is a side view of a rongeur according to some embodiments of the present application. The rongeur 10 comprises a lower shaft 13 and an upper shaft 42, wherein at least a portion of the upper shaft can be removably attached to the lower shaft 13 for easy cleaning. The upper shaft 42 comprises a storage cavity 60 (shown in FIG. 2) that can store bone material from multiple bites of bone.

A handle 20 is operably connected to a proximal portion of the lower shaft 13. The handle 20 comprises a front actuating portion 23 and a back portion 22. Movement of the front actuating portion 23 relative to the back portion 22 (e.g., by exerting a pulling force on the actuating portion 23) of the handle 20 moves the upper shaft 42 relative to the lower shaft 13 (or the lower shaft 13 relative to the upper shaft 42), thereby providing a jaw mechanism that can help remove bone tissue material, as will be discussed further below.

The lower shaft 13 further comprises a raised distal portion 17 extending upwardly from the shaft 13. The raised distal portion 17 can serve as one end of a jaw mechanism designed to bite off and remove bone tissue material, with the distal portion 49 of the upper shaft 42 serving as the other end. When the rongeur bites off bone tissue material from a bone, the material collects in the bone channel 51 that is formed in between the jaw mechanism. As additional bone tissue material is collected in the channel 51, the material will press against the inner wall of the raised distal portion 17 and will collect in the storage cavity 60, as discussed further below.

The upper shaft 42 of the rongeur is slidably connected with the lower shaft 13. The upper shaft 42 includes a distal portion 49 that serves as one part of a jaw mechanism for biting off and removing bone material. In some embodiments, the distal portion 49 of the upper shaft is angled or shaped like a blade to assist in the removal of bone tissue material.

The upper shaft 42 also includes an opening adjacent its distal portion 49 that opens to a storage cavity 60 (shown in FIG. 2) contained therein for collecting bone tissue material. In some embodiments, the storage cavity 60 has a cross-section in the shape of a circle, or square, or rectangle. In some embodiments, the storage cavity has a rectangular cross-section and has a width of between about 4 mm to 8 mm, a height of between about 1 mm to 5 mm, and a length of between about 36 mm to about 44 mm. In some embodiments, the storage cavity 60 has a volume of between about 600 cubic mm to 900 cubic mm, or of about 700 cubic cc. These dimensions provide adequate space to collect bone tissue material, such that multiple bites of bone tissue material can take place before removing the rongeur out of a patient's body. One skilled in the art will appreciate, however, that the storage cavity is not limited to these particular shapes or sizes, and that other designs and dimensions are also possible.

Advantageously, due to the addition of the storage cavity 60, it is possible to take multiple bites of bone using the jaw mechanism formed by the distal portion 17 of the lower shaft and the distal portion 49 of the upper shaft before having to take the rongeur out of the body. In some embodiments, two, three, four, five or more bites of bone can occur before removing the rongeur out of the body. After multiple bites are performed, the rongeur can be removed from the body and the bone tissue material in the storage cavity can be expelled. The addition of the storage cavity 60 thus increases the efficiency of a surgery, and also reduces the risk of contamination by minimizing the amount of exposure of the instrument outside of the patient.

In some embodiments, the upper shaft 42 also includes a slidable internal plunger 52. The distal end of the slidable internal plunger 52 is positioned adjacent to the storage cavity 60. Advantageously, the slidable internal plunger 52 is configured to easily push out and discharge any bone tissue material out of the storage cavity 60. To conveniently operate the slidable internal plunger 52, the upper shaft 42 also includes a finger trigger or hold 45 that can move in a forward and backward, or proximal and distal, direction along a channel 47. In some embodiments, the channel 47 can align with the longitudinal axis of the upper shaft 42. In one example, if the storage cavity 60 is filled with bone tissue material, the slidable internal plunger 52 can be pushed forwardly using a single finger to push outward the slidable internal plunger 52 into the storage cavity 60, thereby helping to push out any bone tissue material from the storage cavity 60. Advantageously, the instrument is configured for one-handed operation, such that one can hold the instrument (e.g., via handle 20) and still operate the finger hold 45 to push out bone material from the storage cavity 60.

Figure 3:
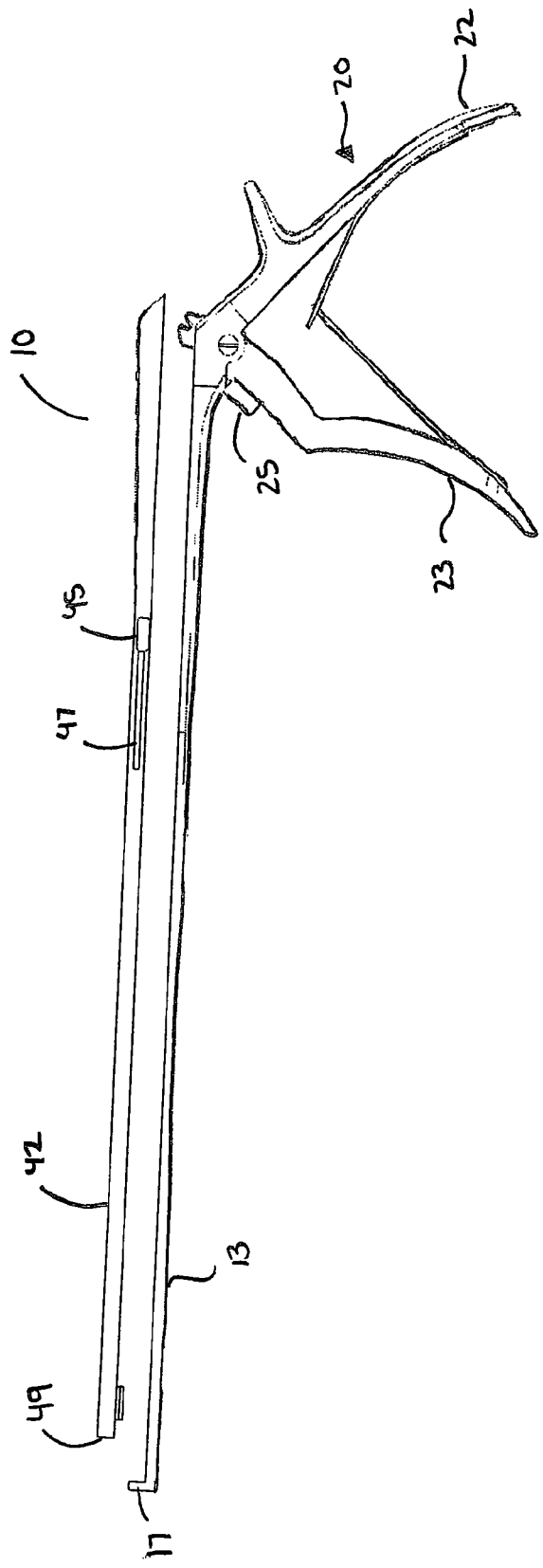
FIG. 3 is a side view of a rongeur with upper shaft having storage cavity detached according to some embodiments of the present application.

The upper shaft 42 can be coupled to the lower shaft 13 using a locking mechanism. In some embodiments, the locking mechanism 25 comprises a knob that can be rotated to detach portions of the upper shaft 42 from the bottom shaft 13. Optionally, a locking latch 26 (shown in FIG. 2) can also be provided to secure the upper shaft 42 and the bottom shaft 13. While the locking mechanism 25 helps to secure the upper shaft 42 to the lower shaft 13, the locking mechanism also advantageously provides a simple means for decoupling or detaching portions of the upper shaft 42 from the lower shaft 13. By detaching the upper shaft 42 from the lower shaft 13, portions of the upper shaft can be easily cleaned, such that the component can be reused if desired. In some embodiments, once the upper shaft 42 is cleaned, detached portions of the upper shaft 42 can be re-attached to the lower shaft 13 so that it can be re-used to bite and store more bone tissue material. In FIG. 3, it is illustrated that the entire upper shaft 42 is completely detachable from the lower shaft 13, in other embodiments, only a portion of the upper shaft 42 is detachable from the lower shaft 13. For example, in some embodiments, the proximal portion of the upper shaft 42 may still be connected to the lower shaft 13 via a hinge mechanism upon unlocking the locking mechanism.

Methods of Use

Various methods can be provided that utilize the rongeurs described above. In some embodiments, the application encompasses methods for treating a subject utilizing an improved rongeur comprising:

a. forming an incision in a body of a patient;
b. inserting a rongeur through the incision, wherein the rongeur includes a jaw mechanism formed by a lower shaft and an upper shaft, and wherein the upper shaft includes a storage cavity adjacent an internal plunger mechanism for dislodging bone tissue material from the storage cavity;
c. removing bone tissue material via the jaw mechanism by taking two or more bites (e.g., three, four, five, or more) out of a bone, wherein at least some of the bone tissue material is deposited within the storage cavity;
d. removing the rongeur from the body of the patient;
e. utilizing the internal plunger mechanism to expel and dispose of any bone tissue material within the storage cavity of the upper shaft;

The process can be repeated multiple times until a desired amount of bone tissue material is removed from the patient. Once the surgical process is completed and when the rongeur needs to be cleaned, the rongeur can be cleaned by detaching the upper shaft including the storage cavity from the lower shaft of the rongeur, cleaning the upper shaft, and re-inserting the rongeur into the patient to remove additional bone tissue material. In addition, one skilled in the art will appreciate that some of the steps can be modified or are otherwise optional.

It will be apparent to those skilled in the art that various modifications and variations can be made in the present invention without departing from the scope or spirit of the invention. Moreover, the improved bone screw assemblies and related methods of use need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone screw assemblies. Thus, it is intended that the present invention cover the modifications and variations of this invention provided that they come within the scope of the appended claims or their equivalents.

What is claimed is:

1. A rongeur comprising:
a handle;
a lower shaft operably connected to the handle;
an upper shaft slidable relative to the lower shaft; and
a locking mechanism configured to couple and decouple the upper shaft from the lower shaft, the locking mechanism being positioned beneath the lower shaft;
wherein the upper shaft has a longitudinal axis and comprises an internal storage cavity for receiving bone tissue material and an internal plunger mechanism with a finger hold,
wherein the internal plunger mechanism extends substantially along the longitudinal axis,
wherein the finger hold is actuated independently from the handle,
wherein the lower shaft includes a raised distal portion,
wherein the internal plunger mechanism is slidable along the longitudinal axis and is configured to push out bone tissue material from the internal storage cavity,
wherein the raised distal portion serves as one end of a jaw mechanism, and
wherein the upper shaft includes a channel formed through an outer surface of the upper shaft, wherein the internal plunger is received within the upper shaft such that a portion of the internal plunger extends through the channel.

2. The rongeur of claim 1, wherein the raised distal portion of the lower shaft and a distal portion of the upper shaft form the jaw mechanism.

3. The rongeur of claim 1, wherein the storage cavity has a width of between about 4 mm to 8 mm.

4. The rongeur of claim 1, wherein the storage cavity has a length of between about 36 mm to about 44 mm.

5. The rongeur of claim 1, wherein a distal end of the internal plunger mechanism is positioned adjacent the internal storage cavity.

6. The rongeur of claim 1, wherein the finger hold of the internal plunger mechanism is located on the upper shaft and is substantially proximate to the handle to allow for one handed operation of the internal plunger mechanism and the handle.

7. The rongeur of claim 6, wherein the finger hold is positioned within a channel that extends along a length of the upper shaft.

8. The rongeur of claim 7, wherein the channel extends along a longitudinal axis of the upper shaft.

9. The rongeur of claim 1, wherein the upper shaft including the internal storage cavity and internal plunger mechanism is detachable from the lower shaft.

10. The rongeur of claim 1, wherein the upper shaft is operably connected to the lower shaft via the locking mechanism.

11. A rongeur comprising:
    a handle having a front actuating portion and a back portion;
    a lower shaft operably connected to the handle;
    an upper shaft slidable relative to the lower shaft; and
    a locking mechanism configured to couple and decouple the upper shaft from the lower shaft, the locking mechanism being positioned beneath the lower shaft;
    wherein the upper shaft has a longitudinal axis and includes an internal storage cavity and an internal plunger mechanism with a finger hold,
    wherein the internal plunger mechanism extends substantially along the longitudinal axis from a proximal portion to a distal portion of the upper shaft,
    wherein the lower shaft includes a raised distal portion,
    wherein the finger hold is actuated independently from the front actuating portion of the handle,
    wherein the raised distal portion serves as one end of a jaw mechanism, and
    wherein the upper shaft includes a channel formed through an outer surface of the upper shaft, wherein the internal plunger is received within the upper shaft such that a portion of the internal plunger extends through the channel.

12. The rongeur of claim 11, wherein the locking mechanism includes a knob that can be rotated for securing the lower shaft to the upper shaft.

13. The rongeur of claim 11, wherein a distal end of the internal plunger mechanism is positioned adjacent a proximal end of the internal storage cavity.

14. The rongeur of claim 11, wherein the lower shaft and the upper shaft form the jaw mechanism for removing bone tissue material.

15. The rongeur of claim 11, wherein the upper shaft including the internal storage cavity and the internal plunger mechanism is attachable and detachable from the lower shaft.

* * * * *